United States Patent [19]

Hope

[11] Patent Number: Plant 5,598

[45] Date of Patent: Dec. 17, 1985

[54] IMPATIENS PLANT NAMED VISTA IMPATIENS NO. 14

[75] Inventor: Claude Hope, Cartago, Costa Rica

[73] Assignee: Pan American Plant Company, Parrish, Fla.

[21] Appl. No.: 566,801

[22] Filed: Dec. 29, 1983

[51] Int. Cl.[4] ..... A01H 5/00
[52] U.S. Cl. ..... Plt./68
[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of impatiens plant known by the cultivar name Vista Impatiens No. 14, and characterized by its intensely brilliant, large orange flowers, profuse year-round flowering even in high light and high temperature conditions, highly variegated foliage that retains its variegation foliage that retains its variegation year-round, vigorous and fast rate of growth, and tall, upright self-branching habit which makes it ideal for bedding plants, pot plant culture and hanging baskets.

1 Drawing Figure

The present invention relates to a new and distinctive cultivar of impatiens plant, botanically known as Impatiens, and known by the cultivar name Vista Impatiens No. 14. The new cultivar was developed from a planned program of hybridization to obtain plants of a wide range of colors and with very large flowers derived from the New Guinea complex of species collected by the Longwood Garden Expedition of 1970. The new cultivar was identified during the breeding and selection process as seedling No. 3473, and was produced from cross breeding seedling No. 3271-1-1-1 (from Impatiens Herzogii P.I. 349584)×1659-2-1-3 (from Impatiens Schlecterii P.I. 354260).

Asexual reproduction by terminal or stem cuttings taken by me at Cartago, Costa Rica has shown that the unique features of this new impatiens are stabilized and are reproduced true to type in successive propagations.

The following characteristics distinguish the new impatiens from both its parent varieties and other cultivated impatiens of this type known and used in the floriculture industry:

1. Vista Impatiens No. 14 was selected and is generally characterized by its variegated foliage, intensely brilliant orange flowers, profuse year-round blooming and vigorous upright habit.

2. Flowers are large (53 mm.), a brilliant orange in color, and do not readily fade. Flowers are borne on long peduncles above the foliage.

3. Flowers are profuse and bloom year-round in Florida, even in periods of high light and temperatures (summer in Florida).

4. Foliage is beautifully variegated, retaining its variegation even in periods of high light and high temperatures.

5. Habit is tall (45–60 cm. when full grown) and upright, making it suitable for bedding plants, pot plant culture and a very full hanging basket.

6. Growth rate is fast and vigorous, producing in 6–8 weeks a saleable plant (30 cm.×40 cm.) in a 5½" pot.

7. Cultivar exhibits good keeping qualities when planted outdoors under full sun (fall, winter and spring) and under light shade in summer in Florida.

8. The new cultivar possesses a good self-branching habit.

The accompanying colored photograph illustrates the overall appearance of the new cultivar, showing the colors as true as it is reasonably possible to obtain in a colored reproduction of this type.

The following is a detailed descrption of my new impatients cultivar based on plants produced under commercial practice in Cortez and Parrish, Fla. The plants were produced outdoors in full sun during the winter, spring and fall months, and under light shade during the summer months. Color references are made to The Royal Horticultural Society Colour Chart except where general terms of ordinary dictionary significance are used.

Parentage: Seedling No. 3271-1-1-1 (from Impatiens Herzogii P.I. 349584)×1659-21-1-3 (from Impatiens Schlecterii P.I. 354260).

Propagation:

A. *Type cutting.*—Tip cutting with 5 cm. stems.

B. *Time to initiate roots.*—10–14 Days at 27° C. summer; 12–16 days at 18° C. winter.

C. *Rooting habit.*—Abundant and fibrous.

Plant description:

A. *Form.*—Tall, upright, dome-shaped.

B. *Habit of growth.*—Rate of growth is fast for this type of plant. Vegetative shoots are formed at lower nodes and flowers at higher nodes.

C. *Foliage description.*—Lower leaves opposite, higher leaves in whorls of 4–6; leaves are simple. (1) Size: Average full grown leaf 100 mm. long×45 mm. wide. Full grown leaves have very short to no petioles. Young leaves have no petioles. (2) Shape: Elliptic, apex acuminate to acute, base attenuate. (3) Texture: Non-leathery, upper surface strigillose. (4) Margin: Ciliate and serrate. (5) Color: Young foliage, top side yellow-orange 17B-C and green 137A; under side yellow-orange 23C and greyed green 191A; mature foliage, top side yellow-orange 18D and green 137B; under side yellow orange 18D and greyed green 191A. (6) Venation: Pinnate, main vein red 47B.

Flowering description:

A. *Flowering habits.*—Very floriferous, flowers occurring progressively around the whorl of leaves. Flowers are single and large.

B. *Natural flowering season.*—Flowering is indeterminate and occurs throughout the year even in periods of high light and high temperatures.

C. *Flower bud description.*—Conical, covered with 3 sepals. Upper 2 sepals are 10 mm. long×5 mm. wide, apex acuminate. Lower sepal is 12 mm. long×10 mm. wide, apex acuminate. All sepals colorless but infused with red. Hollow spur is 51 mm. long (if full grown) and is connected to the base of the lower sepal.

D. *Flowers borne.*—On peduncles 47 mm. long, colorless infused with red.

E. *Quantity of flowers.*—One flower per leaf, occurring progressively around the whorl of leaves.

F. *Petals.*—(1) Shape: Top petal heart-shaped with wide base, all other petals heart-shaped with pointed base. Occasionally a lobe is noted where the petal curves to form top of the heart shape. (2) Color: Top side orange-red 32A (when opening orange red 30B), fading to orange red 33A; under side orange red 30C. (3) Number of petals: Five. (4) Size of flowers: Top petal 17 mm. long×27 mm. wide. Two middle petals 25 mm. long×18 mm. wide; 2 bottom petals 30 mm. long×26 mm. wide. Total flower diameter is 53 mm.

G. *Reproductive organs.*—(1) Stamens: Five; with the lower stamen being shorter than the other stamens. Stamens united in an asymmetrical tube surrounding the ovary. (a) Anther shape: Hooded, cream infused with red. (b) Pollen color: Cream. (2) Pistils: (a) Stigma shape: Five pointed star, colorless. (b) Styles: Very short, reddish in color. (c) Ovaries: 5 celled, 5 mm., green in color.

Disease resistance:

No general plant disease noted. Insect problems can include two-spotted spider mite which can cause foliar injury and thrips which can cause stunting and injury of the growing tip.

I claim:

1. A new and distinct cultivar of impatiens plant known by the cultivar name Vista Impatiens No. 14, as described and illustrated, and characterized by its intensely brilliant, large orange flowers, profuse year-round flowering even in high light and high temperature conditions, highly variegated foliage that retains its variegation year-round, vigorous and fast rate of growth, and tall, upright self-branching habit which makes it ideal for bedding plants, pot plant culture and hanging baskets.

* * * * *

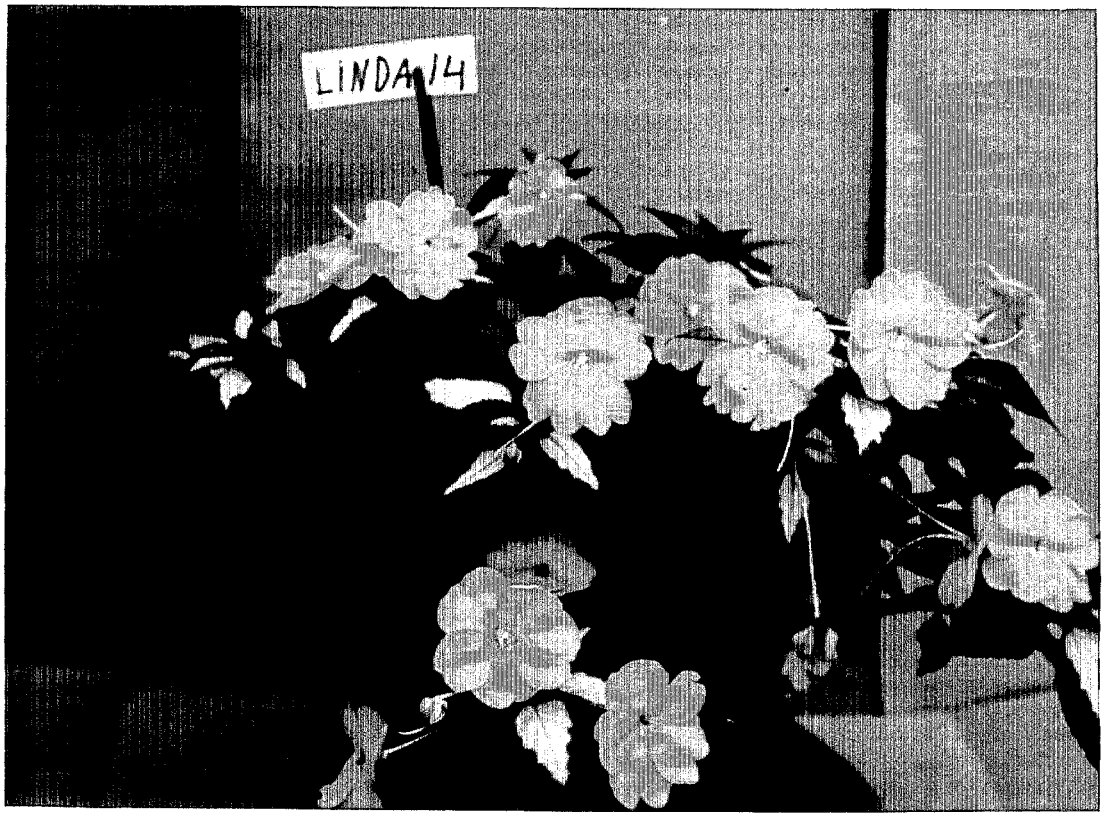
LINDA 14